US009629524B2

United States Patent
Kaneko (10) Patent No.: US 9,629,524 B2
(45) Date of Patent: Apr. 25, 2017

(54) IMAGE PICKUP UNIT FOR ENDOSCOPE HAVING FIRST AND SECOND LEADS WITH DIFFERING DISTANCES TO IMAGE PICKUP DEVICE

(71) Applicant: OLYMPUS CORPORATION, Tokyo (JP)

(72) Inventor: Tomohisa Kaneko, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/791,614

(22) Filed: Jul. 6, 2015

(65) Prior Publication Data

US 2015/0305606 A1    Oct. 29, 2015

Related U.S. Application Data

(63) Continuation of application No. PCT/JP2014/075558, filed on Sep. 26, 2014.

(30) Foreign Application Priority Data

Oct. 4, 2013    (JP) .................................. 2013-209387

(51) Int. Cl.
*H04N 5/374*        (2011.01)
*A61B 1/05*         (2006.01)
(Continued)

(52) U.S. Cl.
CPC ................ *A61B 1/05* (2013.01); *A61B 1/051* (2013.01); *G02B 23/2484* (2013.01);
(Continued)

(58) Field of Classification Search
CPC .............................. A61B 1/05; H04N 5/2251
See application file for complete search history.

(56) References Cited

U.S. PATENT DOCUMENTS 4,895,138 A * 1/1990 Yabe .................. A61B 1/05
                                                348/E5.027
5,050,584 A * 9/1991 Matsuura ........... A61B 1/00068
                                                348/65
(Continued)

FOREIGN PATENT DOCUMENTS

JP      2000-083896 A      3/2000
JP       2000083896      *  3/2000
(Continued)

OTHER PUBLICATIONS

Partial Supplementary European Search Report dated Aug. 17, 2016 in related European Application No. 14 85 1118.1.

*Primary Examiner* — Jay Patel
*Assistant Examiner* — Irfan Habib
(74) *Attorney, Agent, or Firm* — Scully, Scott, Murphy & Presser, P.C.

(57) ABSTRACT

An image pickup unit for endoscope of the invention includes: an image pickup device including on a front face a plurality of electrode pads aligned along one side face; and a circuit substrate having an end face from which a lead group, a distal end portion of which is bonded to the plurality of electrode pads, is extended, wherein the end face of the circuit substrate is disposed more rearward than a rear face of the image pickup device, the lead group includes a first lead constituted of at least one of a lead connected to an image pickup device reference electric potential and a dummy lead which does not include an electrical function, and another second lead, and the first lead is closer to the edge portion where the rear face and the side face of the image pickup device intersect than the second lead is.

4 Claims, 11 Drawing Sheets

(51) Int. Cl.
*G02B 23/24* (2006.01)
*H04N 5/225* (2006.01)
*A61B 1/00* (2006.01)

(52) U.S. Cl.
CPC ......... *H04N 5/2251* (2013.01); *H04N 5/2253* (2013.01); *H04N 5/374* (2013.01); *A61B 1/0011* (2013.01); *A61B 1/00114* (2013.01); *G02B 23/243* (2013.01); *H04N 2005/2255* (2013.01)

(56) References Cited

U.S. PATENT DOCUMENTS

| | | | | |
|---|---|---|---|---|
| 5,291,375 A * | 3/1994 | Mukai | ................... | H05K 1/111 174/259 |
| 5,430,475 A * | 7/1995 | Goto | ................... | H04N 7/18 348/65 |
| 5,868,664 A * | 2/1999 | Speier | ................... | A61B 1/042 348/73 |
| 6,040,612 A * | 3/2000 | Minami | ................... | H01L 27/14618 257/432 |
| 6,095,970 A * | 8/2000 | Hidaka | ................... | A61B 1/00124 600/109 |
| 6,945,929 B2 * | 9/2005 | Ando | ................... | A61B 1/00114 348/45 |
| 7,091,599 B2 * | 8/2006 | Fujimori | ................... | H01L 23/481 257/692 |
| 7,166,537 B2 * | 1/2007 | Jacobsen | ................... | A61B 1/05 438/240 |
| 8,118,732 B2 * | 2/2012 | Banik | ................... | A61B 1/00059 600/117 |
| 8,471,392 B2 * | 6/2013 | Kojima | ................... | A61B 1/05 257/668 |
| 8,520,100 B2 * | 8/2013 | Reshef | ................... | H04N 5/374 348/241 |
| 8,654,184 B2 * | 2/2014 | Murayama | ................... | A61B 1/0008 348/65 |
| 8,666,135 B2 * | 3/2014 | Tomoto | ................... | A61B 1/00009 382/128 |
| 8,876,702 B2 * | 11/2014 | Takahashi | ................... | A61B 1/00114 600/129 |
| 8,944,998 B2 * | 2/2015 | Yamamoto | ................... | A61B 1/051 600/110 |
| 9,037,245 B2 * | 5/2015 | Sharma | ................... | A61B 1/00087 600/104 |
| 9,144,664 B2 * | 9/2015 | Jacobsen | ................... | A61B 1/05 |
| 2007/0270638 A1 * | 11/2007 | Kitano | ................... | A61B 1/00098 600/104 |
| 2009/0268019 A1 | 10/2009 | Ishii et al. | | |
| 2012/0220826 A1 * | 8/2012 | Yamamoto | ................... | A61B 1/051 600/109 |
| 2012/0310043 A1 * | 12/2012 | Hu | ................... | A61B 1/00018 600/109 |

FOREIGN PATENT DOCUMENTS

| | | |
|---|---|---|
| JP | 2001-017389 A | 1/2001 |
| JP | 2005-329093 A | 12/2005 |
| JP | 2008-177701 A | 7/2008 |

* cited by examiner

IMAGE PICKUP UNIT FOR ENDOSCOPE HAVING FIRST AND SECOND LEADS WITH DIFFERING DISTANCES TO IMAGE PICKUP DEVICE

CROSS REFERENCE TO RELATED APPLICATION

This application is a continuation application of PCT/JP2014/075558 filed on Sep. 26, 2014 and claims benefit of Japanese Application No. 2013-209387 filed in Japan on Oct. 4, 2013, the entire contents of which are incorporated herein by this reference.

BACKGROUND OF THE INVENTION

1. Field of the Invention

The present invention relates to an image pickup unit for endoscope in which an image pickup device and a circuit substrate are connected to each other with leads extended from the circuit substrate.

2. Description of the Related Art

In order to observe a site such as inside a living body or structure, which is difficult to be observed, endoscopes have been used in medical and industrial fields, for example, and such endoscopes are configured to be able to be introduced from outside to inside of a living body or structure and include an image pickup unit for picking up an optical image.

An image pickup unit for endoscope includes an objective lens that forms an image of an object, and an image pickup device which is disposed on the image-forming surface of the objective lens and generally called as CCD (charge coupled device), CMOS (complementary metal oxide semiconductor) sensor, or the like.

For example, Japanese Patent Application Laid-Open Publication No. 2008-177701 discloses the image pickup unit for endoscope in which an image pickup device and a circuit substrate disposed on the rear face side of the image pickup device are electrically connected to each other with conductive leads. The leads are extended from the front end portion of the circuit substrate and bonded to electrode pads formed on the front face of the image pickup device on which a light-receiving portion is provided.

In the technique disclosed in the Japanese Patent Application Laid-Open Publication No. 2008-177701, the front end portion of the circuit substrate is protruded more forward than the rear face of the image pickup device on the outside of the side face of the image pickup device, to bring the electrode pads close to the front end portion of the circuit substrate.

SUMMARY OF THE INVENTION

An image pickup unit for endoscope according to one aspect of the present invention includes: an image pickup device including on a front face thereof a plurality of electrode pads aligned along one side face of the image pickup device; and a circuit substrate having an end face from which a lead group is extended, a distal end portion of the lead group being bonded to the plurality of electrode pads, wherein the end face of the circuit substrate is disposed more rearward than a rear face of the image pickup device, the lead group includes a first lead constituted of at least one of a lead connected to an image pickup device reference electric potential and a dummy lead which does not include an electrical function, and another second lead, and a shortest distance between the first lead and an edge portion where the rear face and the side face of the image pickup device intersect is shorter than a shortest distance between the second lead and the edge portion.

DETAILED DESCRIPTION OF THE PREFERRED EMBODIMENTS

Hereinafter, preferred embodiments of the present invention will be described with reference to drawings. Note that, in the drawings used in the description below, a different scale size is used for each of the components in order to allow each of the components to be illustrated in a recognizable size in the drawings, and the present invention is not limited to the number, shapes, ratio of the sizes of the components, and a relative positional relationship among the components shown in these drawings.

First Embodiment

Hereinafter, an example of the embodiment of the present invention will be described. First, with reference to FIG. 1, description will be made on one example of a configuration of an endoscope 101 including an image pickup unit 1 according to the present invention. The endoscope 101 according to the present embodiment is configured to be able to be introduced into a subject such as a human body, and to optically pick up a predetermined site to be observed in the subject. Note that the subject into which the endoscope 101 is introduced is not limited to a human body, but may be another living body or artificial objects such as machines or structures.

Figure 1:
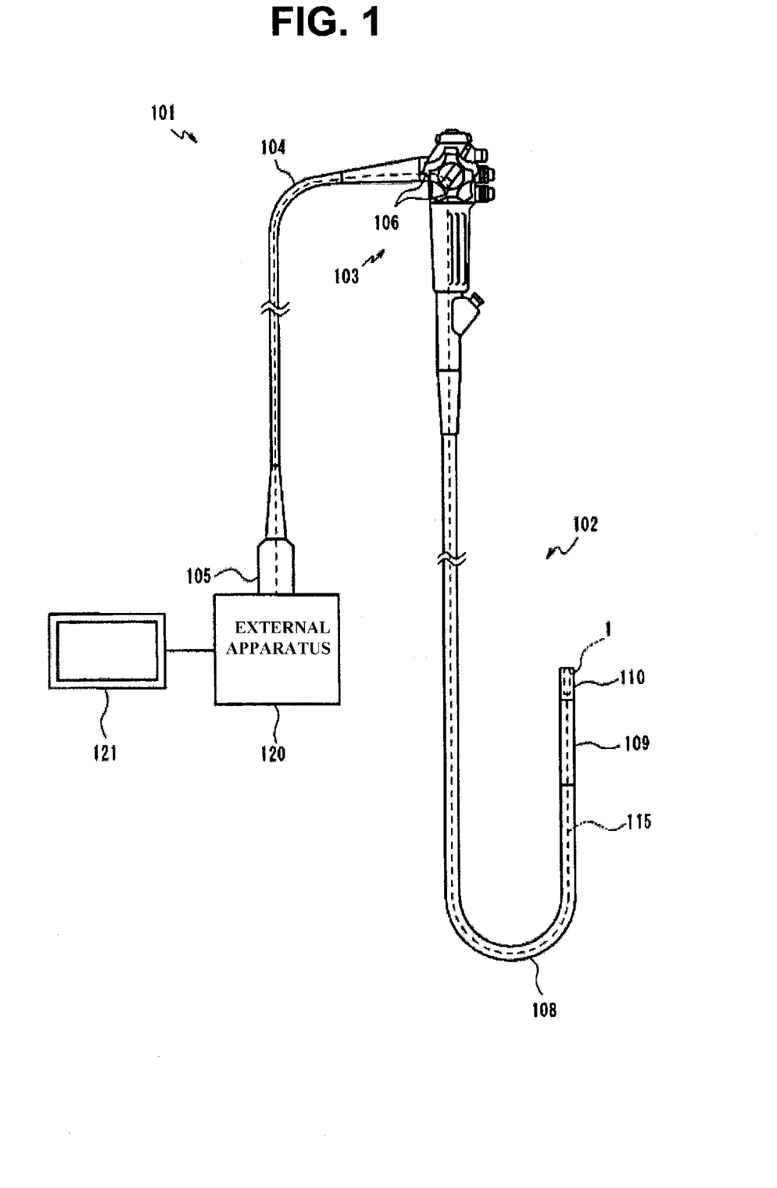
FIG. 1 illustrates a configuration of an endoscope.

The endoscope 101 mainly includes an insertion portion 102 to be introduced into a subject, an operation portion 103 positioned at the proximal end of the insertion portion 102, and a universal cord 104 extended from the side portion of the operation portion 103.

The insertion portion 102 includes the following components in a linked manner a distal end portion 110 disposed at the distal end; a bendable bending portion 109 disposed on the proximal end side of the distal end portion 110; and a flexible tube portion 108 which has flexibility and is disposed on the proximal end side of the bending portion 109 and connected to the distal end side of the operation portion 103. Note that the endoscope 101 may be what is called a rigid endoscope which does not include a flexible part at the insertion portion.

Though details will be described later, the distal end portion 110 is provided with an image pickup unit for endoscope (hereinafter, just referred to as "image pickup unit") 1, and an illumination light emitting portion 113 (not shown in FIG. 1). In addition, the operation portion 103 is provided with an angle operation knob 106 for operating the bending of the bending portion 109.

At the proximal end portion of the universal cord 104, an endoscope connector 105 to be connected to an external apparatus 120 is provided. The external apparatus 120 to which the endoscope connector 105 is connected includes a light source portion, an image processing portion and an image display portion 121, for example.

In addition, the endoscope 101 includes an electric cable 115 and an optical fiber bundle 114 (not shown in FIG. 1) which are inserted through the universal cord 104, the operation portion 103, and the insertion portion 102.

The electric cable 115 is configured to electrically connect the connector portion 105 and the image pickup unit 1. The connector portion 105 is connected to the external apparatus 120, and thereby the image pickup unit 1 is electrically connected to the external apparatus 120 through the electric cable 115. Through the electric cable 115, electric power is supplied from the external apparatus 120 to the image pickup unit 1 and communication is performed between the external apparatus 120 and the image pickup unit 1.

The image processing portion provided in the external apparatus 120 generates a video signal based on an image pickup device output signal outputted from the image pickup unit 1, to output the generated video signal to the image display portion 121. That is, in the present embodiment, the optical image picked up by the image pickup unit 1 is displayed as video on the display portion 121. Note that a part or entirety of the image processing portion and the image display portion 121 may be disposed in the endoscope 101.

In addition, the optical fiber bundle 114 is configured to transmit the light emitted from the light source portion of the external apparatus 120 to the illumination light emitting portion 113 of the distal end portion 110. Note that the light source portion may be disposed at the operation portion 103 or the distal end portion 110 of the endoscope 101.

Figure 2:
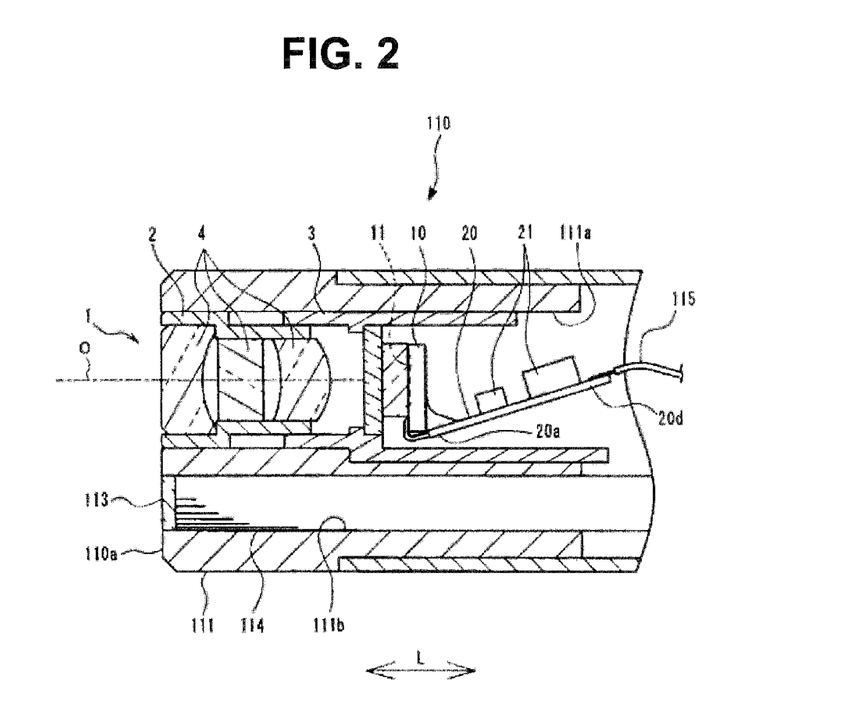
FIG. 2 illustrates a configuration of a distal end portion of the endoscope.

Next, description will be made on the distal end portion 110. As shown in FIG. 2, the distal end portion 110 is provided with the image pickup unit 1 and the illumination light emitting portion 113.

In the present embodiment, as one example, the image pickup unit 1 is disposed so as to pick up an image in the distal end direction along the longitudinal direction (insertion axis direction) of the insertion portion 102 shown by the arrow L in FIG. 2. More specifically, the image pickup unit 1 is disposed such that the optical axis O of an objective lens 4 to be described later is substantially parallel to the longitudinal direction of the insertion portion 102. Note that the image pickup unit 1 may be disposed such that the optical axis O forms a predetermined angle with respect to the longitudinal direction of the insertion portion 102.

In addition, the illumination light emitting portion 113 is configured to emit light entered from the optical fiber bundle 114 so as to illuminate the object of the image pickup unit 1. In the present embodiment, the illumination light emitting portion 113 is configured to emit light from the distal end surface of the distal end portion 110 toward the distal end direction along the longitudinal direction of the insertion portion 102.

The image pickup unit 1 and the illumination light emitting portion 113 are held by a holding portion 111 provided at the distal end portion 110. The holding portion 111 is a rigid member exposed on a distal end surface 110a of the distal end portion 110, and provided with through holes 111a, 111b drilled along the longitudinal direction of the insertion portion 102.

Inside the through holes 111a, 111b, the image pickup unit 1 and the illumination light emitting portion 113 are fixed with adhesive, by screwing, or the like. Furthermore, the optical fiber bundle 114 is inserted from the proximal end side into the through hole 111b to be fixed thereto.

Next, description will be made on the configuration of the image pickup unit 1 according to the present embodiment. As shown in FIG. 2, the image pickup unit 1 includes the objective lens 4, an image pickup device 10, and the circuit substrate 20. These members which constitute the image pickup unit 1 are held by a substantially barrel-shaped holding frame 3. In the present embodiment, the holding frame 3 is a cylindrical-shaped member which surrounds around the optical axis O.

Hereinafter, the direction from the image pickup unit 1 toward the object along the optical axis O of the image pickup unit 1 (left side in FIG. 2) is referred to as a front side and the opposite direction of the above-described direction is referred to as a rear side.

The objective lens 4 is disposed in a cylindrical-shaped lens barrel 2, and constituted of an optical member such as one or a plurality of lenses for forming an image of the object on the light-receiving portion 11 of the image pickup device 10 to be described later. The lens barrel 2 is fitted in the holding frame 3 from the front side, to be fixed therein with adhesive or the like. Note that the objective lens 4 may include an optical element such as a reflector, a prism, an optical filter, or the like. In addition, the objective lens 4 may have a configuration in which the focal length is variable.

The image pickup device 10 and the circuit substrate 20 are electrically connected to each other with the configuration to be detailed later. The image pickup device 10 and the circuit substrate 20 are fixed in the holding frame 3 after the relative positions between the image pickup device 10 and the circuit substrate 20 have been fixed with adhesives 40, 41. In addition, the electric cable 115 is connected to the rear portion of the circuit substrate 20. Furthermore, electronic components 21 which constitute electric circuits are mounted on the circuit substrate 20, as shown in the drawings.

Figure 3:
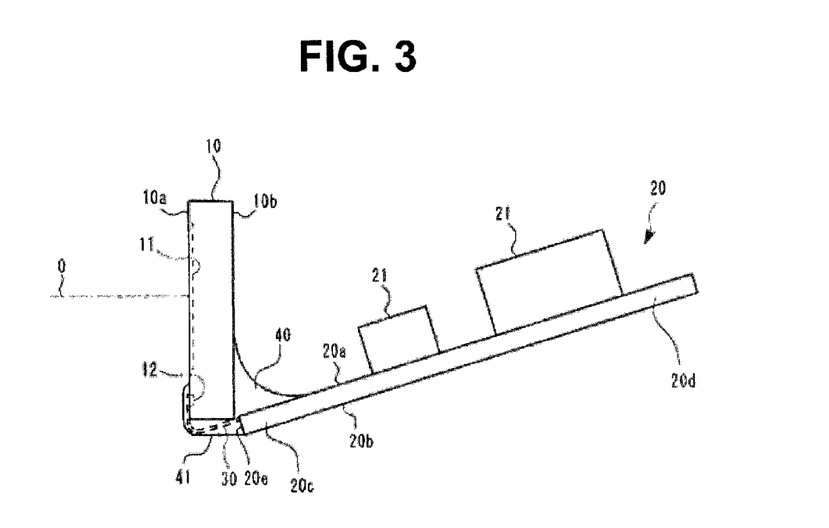
FIG. 3 is a side view showing only an image pickup device and a circuit substrate.
Figure 4:
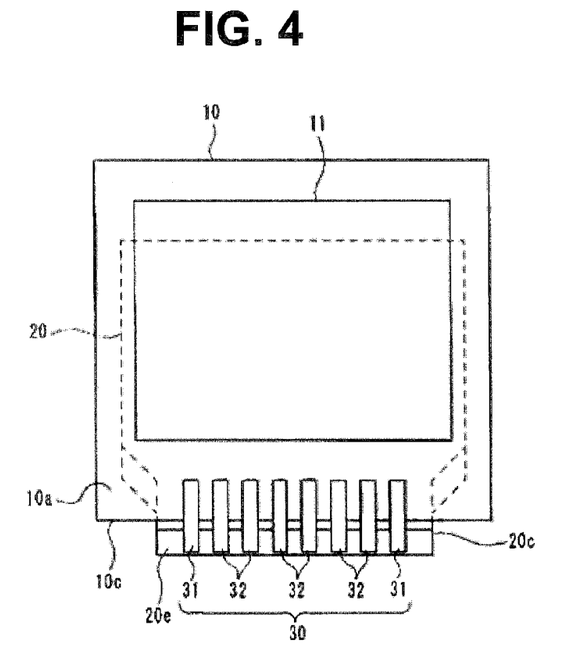
FIG. 4 is a front view of the image pickup device and the circuit substrate viewed from a direction facing a front face of the image pickup device.
Figure 5:
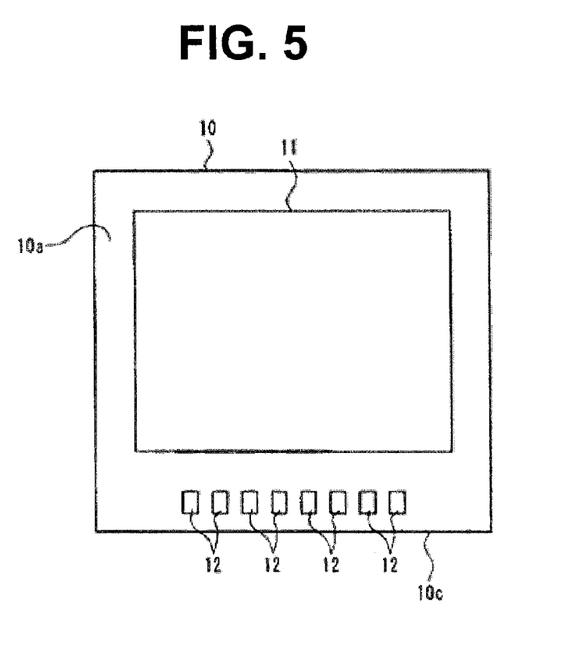
FIG. 5 is a front view showing only the image pickup device viewed from the direction facing the front face.

Hereinafter, description will be made on the detailed configuration of the electric connection between the image pickup device 10 and the circuit substrate 20 in the image pickup unit 1. FIG. 3 is a side view which only extracts and shows the image pickup device 10 and the circuit substrate 20 in the image pickup unit 1. FIG. 4 is a front view of the image pickup device 10 and the circuit substrate 20 viewed from the direction facing a front face 10a. FIG. 5 is a front view showing only the image pickup device 10 to which a lead group 30 is not bonded, viewed from the direction facing the front face 10a.

Hereinafter, the face of the image pickup device 10 on which the light-receiving portion 11 is provided is referred to as the front face 10a and the face of the image pickup device 10 which is opposite side of the light-receiving portion 11 is referred to as the rear face 10b.

The image pickup device 10 includes the light-receiving portion 11 constituted of a plurality of aligned photodiodes which receive the light passed through the objective lens 4 and perform photoelectric conversion on the received light, and an image pickup device of a type generally called as CCD (charge coupled device) or CMOS (complementary metal oxide semiconductor) image sensor, or image pickup devices of other various types can be applied as the image pickup device 10. In the present embodiment, the image pickup device 10 is disposed in the image pickup unit 1 such that the front face 10a is perpendicular to the optical axis O.

As shown in FIG. 5, the image pickup device 10 has a planar parallelogram outer shape when viewed from the direction facing the front face 10a. On the front face 10a of the image pickup device 10, the light-receiving portion 11 and a plurality of electrode pads 12 are formed.

The plurality of electrode pads 12 are parts electrically connected to the electric circuit formed in the image pickup device 10. The plurality of electrode pads 12 are aligned along one side face 10c in the vicinity of the outside edge portion of the front face 10a when viewing the image pickup device 10 so as to face the front face 10a.

As shown in FIG. 4, the distal end portion of the lead group 30 constituted of a plurality of metal leads to be described later is bonded to each of the electrode pads 12. The lead group 30 is extended from the circuit substrate 20. The plurality of electrode pads 12 and the electric circuits formed on the circuit substrate 20 are electrically connected to each other by the lead group 30.

Although the method of bonding the plurality of electrode pads 12 and the lead group 30 is not specifically limited, the method of bonding the electrode pads of an IC and the inner leads, which is used in the Tape automated bonding (TAB) process, can be applied, for example. In the TAB process, gold bumps or soldering bumps are formed on the electrode pads of the IC, and the leads are thermo-compressed on the bumps. Note that the method of bonding the plurality of electrode pads 12 and the lead group 30 is not limited to this method, and the method of thermo-compressing the electrode pads 12 and the lead group 30 without the use of the bumps, the method of using anisotropic conductive resin, or the like may be used.

The circuit substrate 20 is disposed at the rear of the image pickup device 10. The circuit substrate 20 includes a conductive layer made of a conductive material such as metallic foil at the plate-shaped or film-shaped substrate portion made of electric insulating material, and the conductive layer forms an electronic circuit pattern. In addition, a resist layer made of an electric insulating material is formed on the conductive layer, as needed.

The circuit substrate 20 may be configured such that the conductive layer is formed on one or both faces of the one substrate portion, or may include three or more conductive layers in which a plurality of substrate portions and the conductive layers are stacked alternately. In the present embodiment, as one example, the circuit substrate 20 is what is called a flexible printed circuit substrate in which the substrate portion is made of a flexible material, and has a configuration of two-layer circuit substrate in which the conductive layer is provided both on a first face 20a side and a second face 20b side of the single substrate portion.

The circuit substrate 20 is disposed at the rear of the image pickup device 10 so as to extend in the front-back direction. A front end portion 20c of the circuit substrate 20 is located at a position which is more rearward than the rear face 10b of the image pickup device 10 and which is in the vicinity of the side face 10c of the image pickup device 10. That is, the front end portion 20c of the circuit substrate 20 is located away from the optical axis O in the radial direction.

Figure 6:
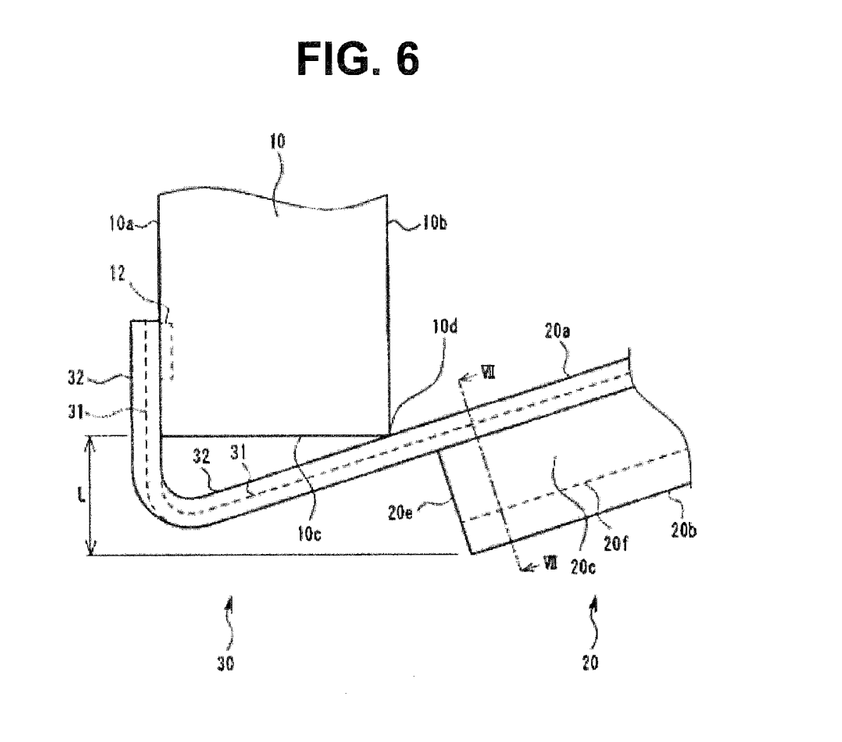
FIG. 6 is a side view showing a detail of a configuration of a lead group.

An end face 20e of the front end portion 20c of the circuit substrate 20 is arranged so as to extend along an edge portion 10d where the rear face 10b and the side face 10c of the image pickup device 10 intersect. In the present embodiment, as shown in FIG. 4 and FIG. 6, the end face 20e of the front end portion 20c of the circuit substrate 20 is parallel to the extending direction of the edge portion 10d of the image pickup device 10.

Hereinafter, with regard to the front end portion 20c of the circuit substrate 20, the face which is on the side opposed to (close to) the optical axis O is referred to as the first face 20a and the face which is opposite of the first face 20a is referred to as the second face 20b. That is, the first face 20a is the surface close to the central axis of the image pickup unit 1.

At the front end portion 20c of the circuit substrate 20, the lead group 30, which is constituted of a plurality of leads protruded in parallel from the end face 20e, is provided. Each distal end portion of the leads in the lead group 30 is bonded to each of the plurality of electrode pads 12 of the above-described image pickup device 10.

In the present embodiment, the respective leads which constitute the lead group 30 are formed by the conductive layers of the circuit substrate 20 being extended more outward than the outside edge of the substrate portion. The leads, which are thus formed by extending the conductive layers constituting electronic circuits in the circuit substrate 20 more outward than the outside edge of the substrate portion, are generally referred to as flying leads, inner leads, or the like.

The end face 20e of the circuit substrate 20, from which the lead group 30 is extended, is located more rearward than the rear face 10b of the image pickup device 10. Therefore, the lead group 30 is disposed in a shape curved from the rear face 10b side of the image pickup device 10 toward the front face 10a side so as to wrap around the outside of the side face 10c.

Hereinafter, description will be made on the detailed configuration of the lead group 30. The lead group 30 is composed of a first lead 31 which includes one or more leads and a second lead 32 which includes a plurality of leads.

The first lead 31 is electrically connected to a circuit having the same electric potential as that of the rear face 10b and the side face of the image pickup device 10 in the image pickup unit 1. The rear face 10b and the side face of the image pickup device 10 are the points at which the electric potential is referred to as the image pickup device reference electric potential. Therefore, the first lead 31 is electrically connected to the circuit on the circuit substrate 20, the electric potential of the circuit being referred to as the image pickup device reference electric potential.

More specifically, the first lead 31 is a lead, the distal end portion of which is bonded to the electrode pad 12 used as the image pickup device reference electric potential, and the first lead 31 is electrically connected to the circuit on the circuit substrate 20, the electric potential of the circuit being equal to the image pickup device reference electric potential. The electrode pad 12 to which the first lead 31 is bonded is electrically connected to the rear face 10b and side face of the image pickup device 10.

Note that a part of or all of the one or more first leads 31 may be a dummy lead or dummy leads which do not have a function related to electric connection between the image pickup device 10 and the circuit substrate 20. When all of the first leads 31 are the dummy leads, the circuit of the circuit substrate 20, the electric potential of which is used as the image pickup device reference electric potential, is electrically connected to the image pickup device 10 with the second leads 32. Note that, preferably, the first lead 31 as the dummy lead is electrically connected to the circuit of the circuit substrate 20, the electric potential of the circuit being used as the image pickup device reference electric potential.

The second leads 32 electrically connect the electrode pads 12 other than the electrode pad 12 to which the first lead 31 is connected and the electric circuit formed on the circuit substrate 20. That is, the second leads 32 include at least all the leads bonded to the electrode pads 12 for input and output of the signals from the image pickup device 10. Note that the second leads 32 may include the lead, the electric potential of which is used as the image pickup device reference electric potential.

In the present embodiment, the shortest separation distance between the first lead 31 and the edge portion 10d where the rear face 10b and the side face 10c of the image pickup device 10 intersect is shorter than the shortest separation distance between all of the second leads 32 and the edge portion 10d. In addition, the first lead 31 may contact the edge portion 10d or the side face 10c.

The configuration for arranging the first lead 31 closer to the edge portion 10d as compared with the second leads 32 is not specifically limited.

Figure 7:
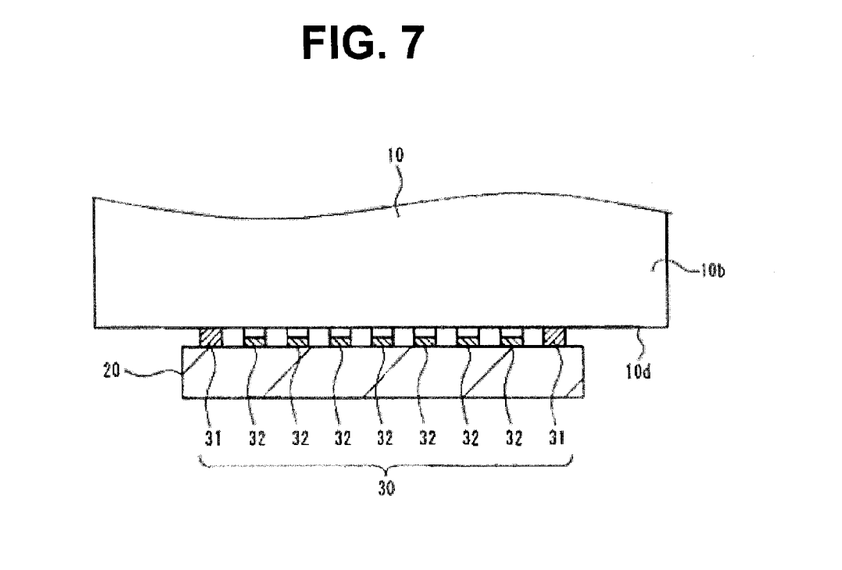
FIG. 7 is a cross-sectional view taken along the VII-VII line in FIG. 6.

As one example, in the present embodiment shown in FIGS. 6 and 7, the first leads 31 and the second leads 32 are formed by the conductive layers arranged on the first face 20a side of the circuit substrate 20, and the thickness T1 of the conductive layer constituting the first leads 31 is configured to be thicker than the thickness T2 of the conductive layer constituting the second leads 32. Note that FIGS. 6 and 7 omit the illustration of the resist layer of the circuit substrate 20, and adhesives 40, 41 for description.

Since the conductive layer constituting the first leads 31 and the conductive layer constituting the second leads 32 are formed on the surface on the first face 20a side of the same substrate portion 20f, the first leads 31 formed by the thicker conductive layer are closer to the edge portion 10d than the second leads 32 are to the edge portion 10d. Note that the first leads 31 contact the edge portion 10d in the present embodiment shown in the drawings.

The relative position between the image pickup device 10 and the circuit substrate 20 is fixed by the adhesives 40 and 41, with the image pickup device 10 and the circuit substrate 20 being connected to each other by the above-described lead group 30. The adhesive 40 bonds the rear face 10b of the image pickup device 10 and the first face 20a of the circuit substrate 20, and the adhesive 41 bonds the side face 10c of the image pickup device 10 and the end face 20e of the circuit substrate 20.

As described above, the image pickup unit 1 according to the present embodiment includes the image pickup device 10 including, on the front face 10a, the plurality of electrode pads 12 aligned along the one side face 10c, and the circuit substrate 20 having the end face 20e from which the lead group 30 is extended, the distal end portion of the lead group 30 being bonded to the plurality of electrode pads 12. The end face 20e of the circuit substrate 20 is disposed more rearward than the rear face 10b of the image pickup device 10.

In addition, in the present embodiment, the lead group 30 is configured by one or a plurality of first leads 31 which are constituted of the lead connected to the image pickup device reference electric potential and/or the dummy lead which does not have the electrical function, and other second leads 32. The shortest distance between the first leads 31 and the edge portion 10d where the rear face 10b and the side face 10c of the image pickup device 10 intersect is shorter than the shortest distance between all the second leads 32 and the edge portion 10d.

The first leads 31 configured by the lead connected to the image pickup device reference electric potential and/or the dummy lead which does not have the electrical function are thus arranged so as to be closer to the edge portion 10d than the second leads used for transmitting electric signals are to the edge portion 10d. Therefore, when the lead group 30 gets close to the edge portion 10d, the first leads 31 first contact the side face 10c and the rear face 10b of the image pickup device 10, which prevents the second leads 32 from contacting the side face 10c and the rear face 10b of the image pickup device 10. Since the electric potentials at the side face 10c and the rear face 10b are taken as the image pickup device reference electric potential, there is no problem even if the side face 10c and the rear face 10b of the image pickup device 10 are in contact with the first lead 31.

Therefore, according to the present embodiment, even if the front end portion 20c of the circuit substrate 20 is arranged on the inner side in the radial direction (direction of getting close to the optical axis O) and the lead group 30 is brought close to the side face 10c and the edge portion 10d of the image pickup device 10, it is possible to prevent the second leads 32 for transmitting signals from contacting the side face 10c and the rear face 10b of the image pickup device 10. Therefore, according to the present embodiment, when the image pickup device 10 is viewed from the direction facing the front face 10a (viewed from the direction along the optical axis O), the amounts of outward protrusion (shown by the reference sign L in FIG. 7) of the circuit substrate 20 and the lead group 30 from the outer shape of the image pickup device 10 can be reduced, thereby achieving the reduced diameter of the image pickup unit 1.

Figure 8:
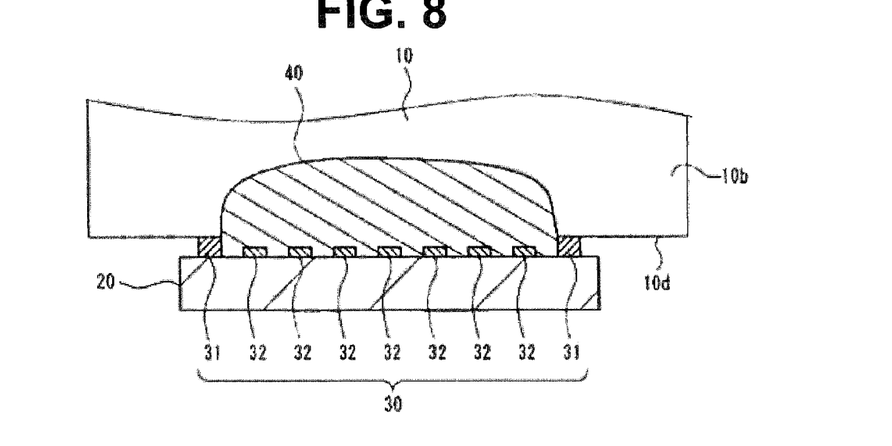
FIG. 8 illustrates a state where adhesive is applied on a rear face of the image pickup device and a first face of the circuit substrate.

In addition, in the present embodiment, the outermost two leads of the lead group 30 are the first leads 31. That is, each of the pair of the thicker first leads 31 is arranged on each side of a group of thinner second leads 32. According to such a configuration, the adhesive 40 is applied to the region enclosed by the pair of the first leads 31 as shown in FIG. 8, thereby reducing unevenness of the application amount and application region of the adhesive 40. It is preferable that the application amount of the adhesive 40 has less unevenness and is stable, since the application amount affects the strength for fixing the image pickup device 10 and the circuit substrate 20.

Figure 9:
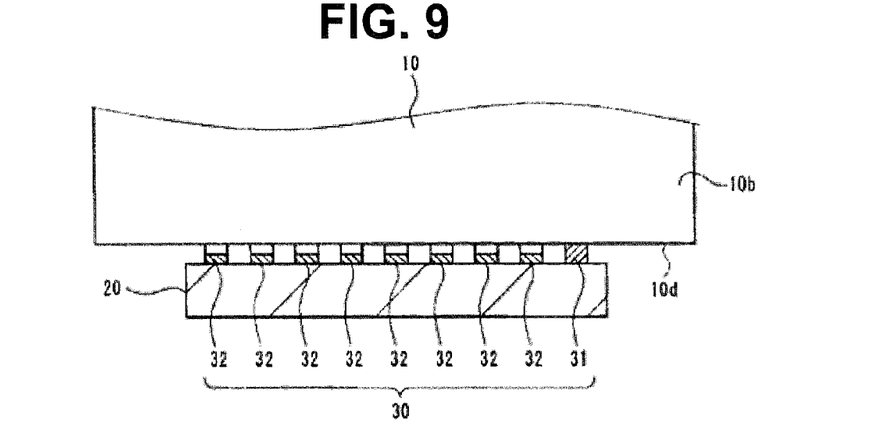
FIG. 9 illustrates a first modified example of a first embodiment.
Figure 10:
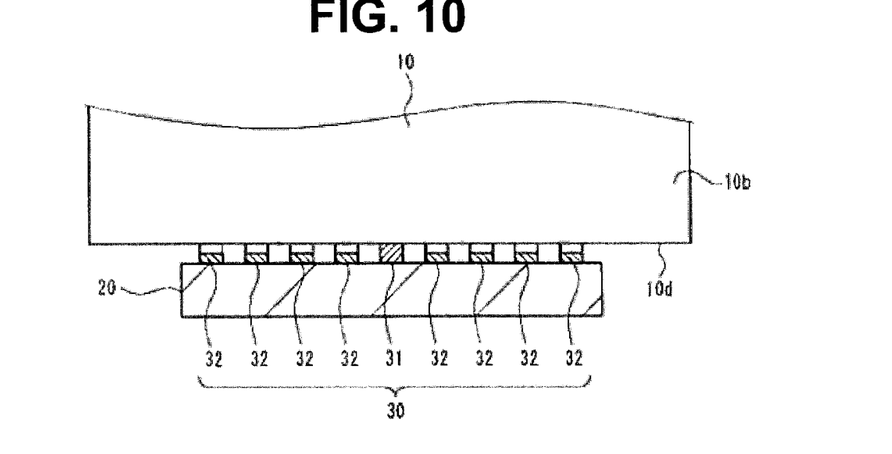
FIG. 10 illustrates a second modified example of the first embodiment.

Note that, in the present embodiment shown in the drawings, the number of the first leads 31 is two, and the first leads are disposed respectively on the both outer sides of the lead group 30. However, the number and the positions of the first leads 31 are not limited to the above-described number and positions. For example, as shown in FIG. 9, one first lead 31 may be disposed on the one of the outer sides of the lead group 30. In addition, as shown in FIG. 10 for example, the first lead 31 may be disposed on the inner side of the lead group 30. The modified examples shown in FIGS. 9 and 10 are also capable of preventing the second leads 32 for transmitting signals from contacting the side face 10c and the rear face 10b of the image pickup device 10, as described above.

Second Embodiment

Next, the second embodiment of the present invention will be described. Hereinafter, only the points different from the first embodiment will be described. The same constituent elements as those in the first embodiment will be attached with the same reference numerals and description thereof will be appropriately omitted.

In the above-described first embodiment, the thickness of the conductive layer constituting the first lead 31 is made greater than that of the conductive layer constituting the second leads 32, thereby bringing the first lead 31 closer to the edge portion 10d of the image pickup device 10 than the second leads to the edge portion 10d. However, the configuration for bringing the first lead 31 closer to the edge portion 10d of the image pickup device 10 than the second leads to the edge portion 10d is not limited to the one employed in the first embodiment. The present embodiment is different from the first embodiment in the configuration for bringing the first lead 31 closer to the edge portion 10d of the image pickup device 10 than the second leads 32 to the edge portion 10d.

Figure 11:
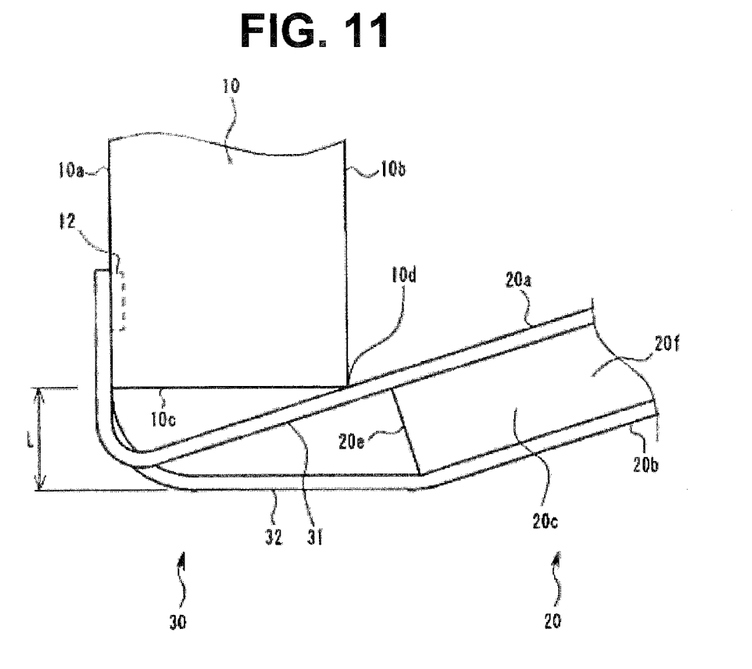
FIG. 11 is a side view showing a detail of a configuration of a lead group according to a second embodiment.

As shown in FIG. 11, in the present embodiment, the first lead 31 is configured by the conductive layer provided on the first face 20a side of the circuit substrate 20 and the second leads 32 are configured by the conductive layer provided on the second face 20b side of the circuit substrate 20.

Note that the conductive layer provided on the first face 20a side of the circuit substrate 20 may have the same thickness as or a different thickness from that of the conductive layer provided on the second face 20b side of the circuit substrate 20.

In the above-described present embodiment, an electric insulating substrate portion 20f is interposed between the conductive layer provided on the first face 20a side of the circuit substrate 20 and the conductive layer provided on the second face 20b side, which allows the first lead 31 to be closer to the edge portion 10d of the image pickup device 10 by the thickness of the substrate portion 20f than the second leads 32 are to the edge portion 10d.

Also in the present embodiment, similarly as in the first embodiment, even if the front end portion 20c of the circuit substrate 20 is arranged on the inner side in the radial direction at the position more rearward than the rear face 20b of the image pickup device 10, and the lead group 30 is brought close to the side face 10c and edge portion 10d of the image pickup device 10, it is possible to prevent the second leads 32 for transmitting signals from contacting the side face 10c and rear face 10b of the image pickup device 10. Therefore, according to the present embodiment, when the image pickup device 10 is viewed from the direction facing the front face 10a, the amounts of outward protrusion (shown by the reference sign L in FIG. 11) of the circuit substrate 20 and the lead group 30 from the outer shape of the image pickup device 10 can be reduced, thereby achieving the reduced diameter of the image pickup unit 1.

Third Embodiment

Next, the third embodiment of the present invention will be described. Hereinafter, only the points different from the first embodiment will be described. The same constituent elements as those in the first embodiment will be attached with the same reference numerals and description thereof will be appropriately omitted.

The present embodiment is different from the first embodiment in the configuration for bringing the first leads 31 closer to the edge portion 10d of the image pickup device 10 than the second leads 32 to the edge portion 10d.

Figure 12:
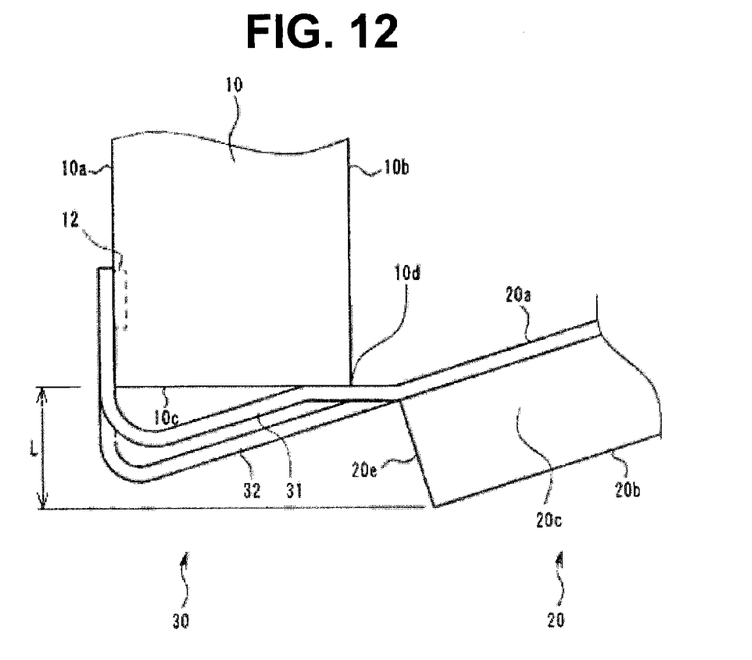
FIG. 12 is a side view showing a detail of a configuration of a lead group according to a third embodiment.

As shown in FIG. 12, in the present embodiment, the first lead 31 and the second leads 32 are configured by the same conductive layer provided on the first face 20a side of the circuit substrate 20. The first lead 31 extends from the end face 20e to be bent so as to reach the electrode pad 12 through the route closer to the edge portion 10d of the image pickup device 10 than the route of the second leads 32 is to the edge portion 10d.

Specifically, the second leads 32 extend forward from the end face 20e along the first face 20a of the circuit substrate 20, and the first lead 31 extends from the end face 20e to be bent in the direction contacting the edge portion 10d, and thereafter extends forward.

Also in the above-described present embodiment, similarly as in the first embodiment, even if the front end portion 20c of the circuit substrate 20 is arranged on the inner side in the radial direction at the position more rearward than the rear face 20b of the image pickup device 10, and the lead group 30 is brought close to the side face 10c and the edge portion 10d of the image pickup device 10, it is possible to prevent the second leads 32 for transmitting signals from contacting the side face 10c and rear face 10b of the image pickup device 10. Therefore, according to the present embodiment, when the image pickup device 10 is viewed from the direction facing the front face 10a, the amounts of outward protrusion (shown by the reference sign L in FIG. 12) of the circuit substrate 20 and the lead group 30 from the outer shape of the image pickup device 10 can be reduced, thereby achieving the reduced diameter of the image pickup unit 1.

The method for configuring the first lead 31 and the second leads 32 so as to take different routes from the end face 20e to the electrode pads 12 is not specifically limited as disclosed in the present embodiment. Hereinafter, description will be made on an example of a method for rendering the bent shapes of the first leads 31 and the second leads 32 different.

Figure 13:
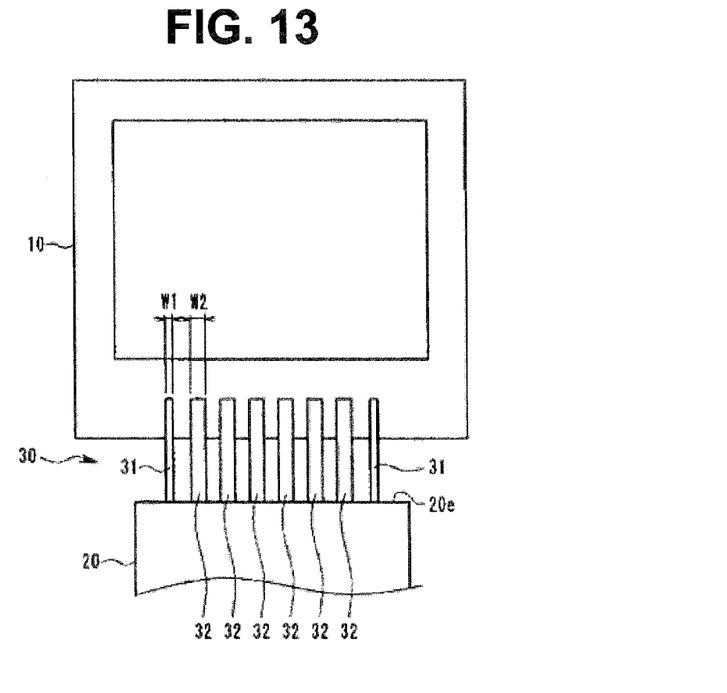
FIG. 13 illustrates a method of forming the lead group in the third embodiment.
Figure 14:
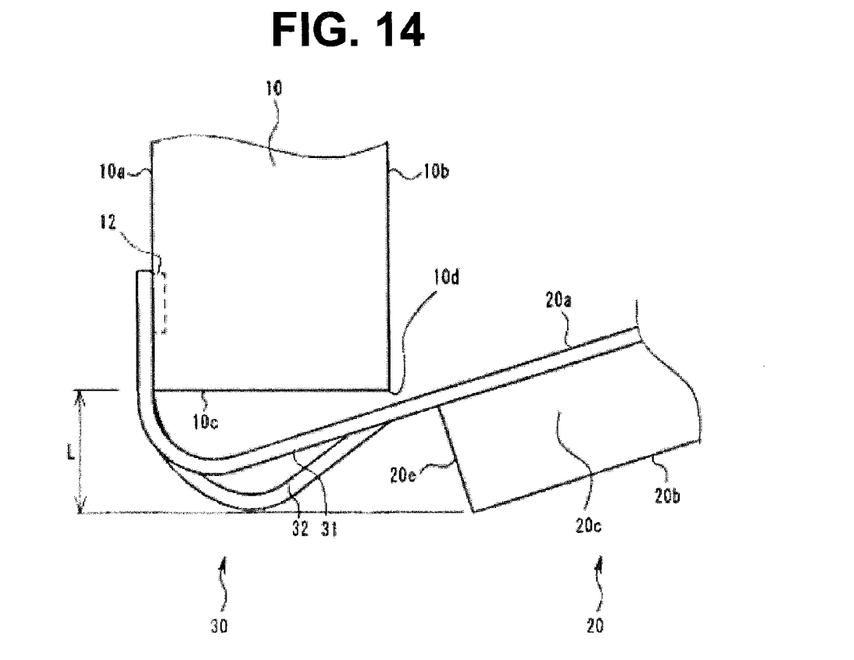
FIG. 14 illustrates a method of forming the lead group in the third embodiment.

For example, as shown in FIG. 13, if the width W1 of the first leads 31 is made narrower than the width W2 of the second leads 32, the radius of curvature of the second leads 32 becomes larger than that of the first leads 31 when the lead group 30 is bent. Therefore, as shown in FIG. 14, the first leads 31 are closer to the side face 10c and the edge portion 10d of the image pickup device 10 than the second leads 32 are to the side face 10c and the edge portion 10d. Note that, in the examples shown in FIGS. 13 and 14, each of the first leads 31 may be configured such that only a part in the extending direction has a width narrower than that of the second leads 32.

Figure 15:
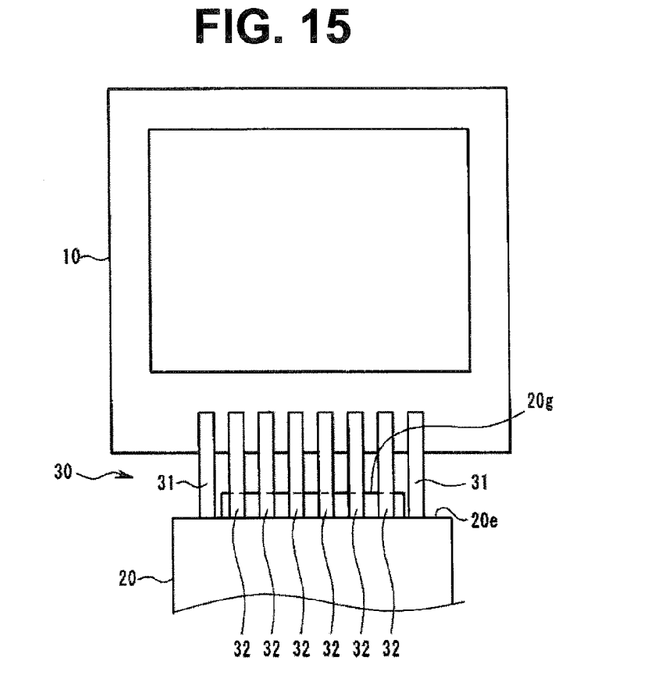
FIG. 15 illustrates a method of forming the lead group in the third embodiment.
Figure 16:
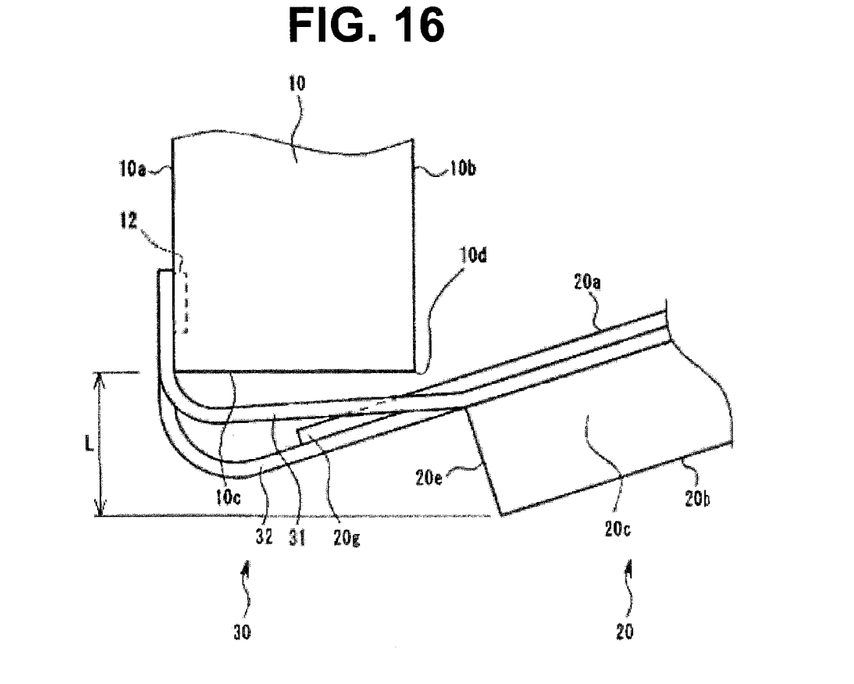
FIG. 16 illustrates a method of forming the lead group in the third embodiment.

In addition, for example, as shown in FIG. 15, if a bending forming member 20g made of an electric insulating material and extended from the end face 20e is disposed on the side of the faces, which are to be bonded to the electrode pads 12, of the second leads 32, after the bending processing of the lead group 30, as shown in FIG. 16, each of the first leads 31 is closer to the side face 10c and the edge portion 10d of the image pickup device 10 than the second leads 32 are to the side face 10c and the edge portion 10d.

The bending forming member 20g can be formed by extending the substrate portion or the resist disposed on the more first face 20a side than the conductive layers constituting the first leads 31 and the second leads 32.

Figure 17:
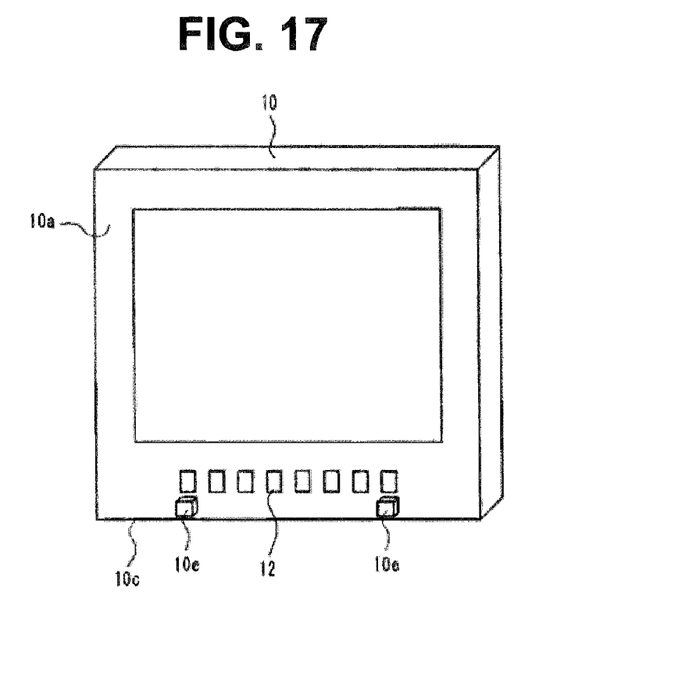
FIG. 17 illustrates a method of forming the lead group in the third embodiment.
Figure 18:
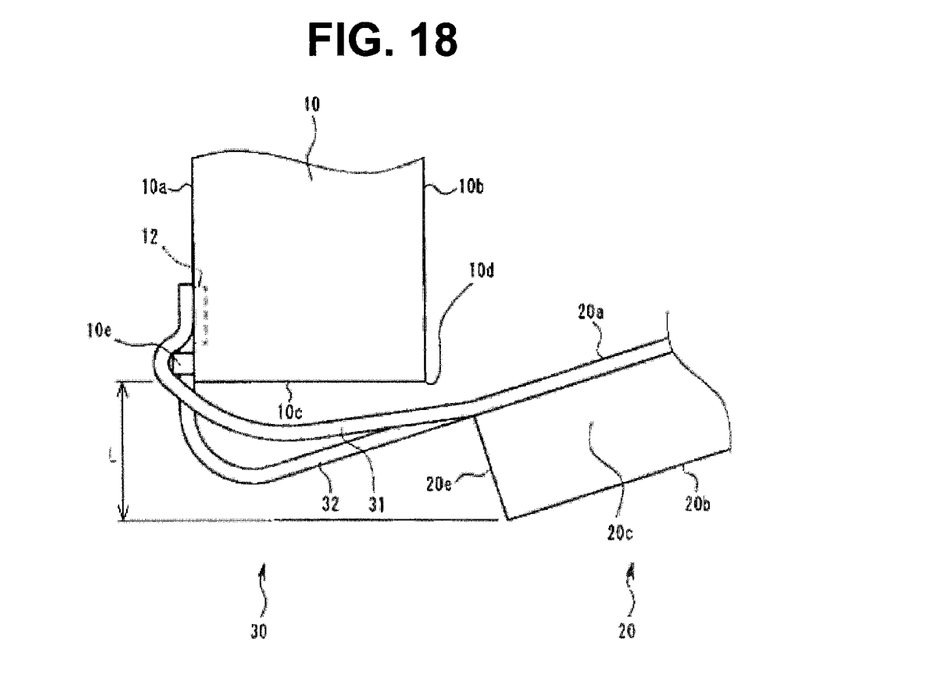
FIG. 18 illustrates a method of forming the lead group in the third embodiment.

In addition, for example, as shown in FIG. 17, bending forming members 10g can be provided to the image pickup device 10. In the example shown in FIG. 17, protruded bending forming members 10g are provided at positions closer to the side face 10c than the electrode pads 12 to which the first leads 31 are bonded are to the side face 10c. The first leads 31 are bonded to the electrode pads 12 by passing outside the bending forming members 10g. Therefore, as shown in FIG. 18, the first leads 31 takes the route closer to the side face 10c and the edge portion 10d of the image pickup device 10, compared with the route of the second leads 32.

Figure 19:
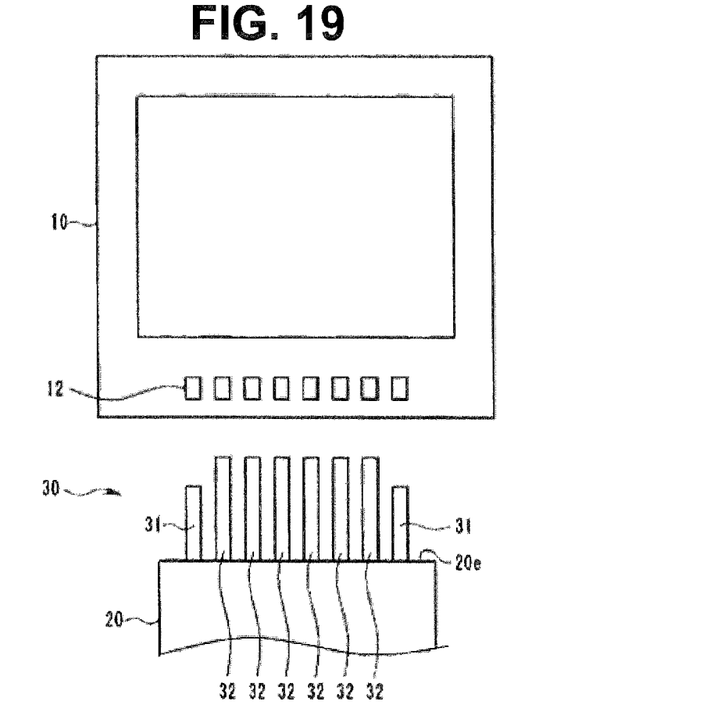
FIG. 19 illustrates a method of forming the lead group in the third embodiment.
Figure 20:
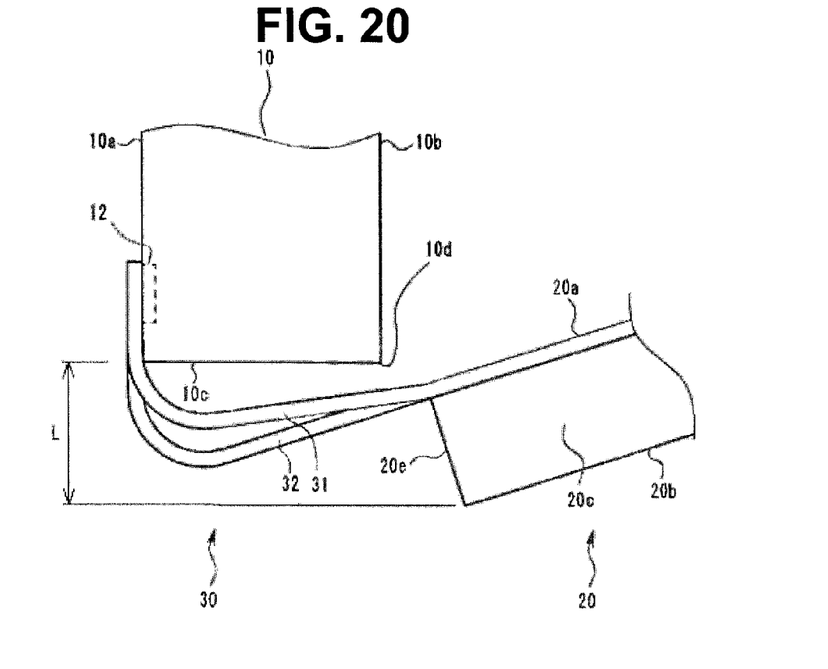
FIG. 20 illustrates a method of forming the lead group in the third embodiment.

In addition, for example, as shown in FIG. 19, if the extending length of each of the first leads 31 from the end face 20e is set to be shorter than the extending length of the second leads 32, the first leads 31 take the route closer to the side face 10c and the edge portion 10d of the image pickup device 10, compared with the route of the second leads 32, as shown in FIG. 20.

Fourth Embodiment

Next, description will be made on the fourth embodiment of the present invention. Hereinafter, only the points different from the first embodiment will be described. The same constituent elements as those in the first embodiment will be attached with the same reference numerals and description thereof will be appropriately omitted.

Figure 21:
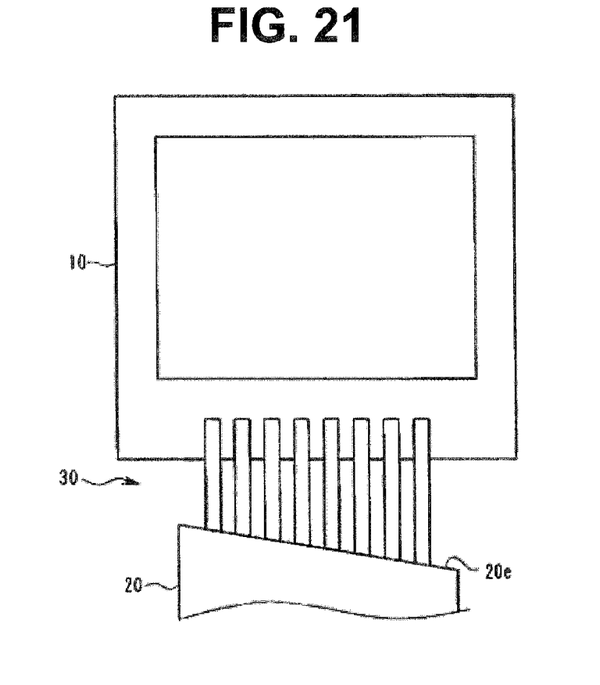
FIG. 21 illustrates a shape of an end face of a circuit substrate according to a fourth embodiment.
Figure 22:
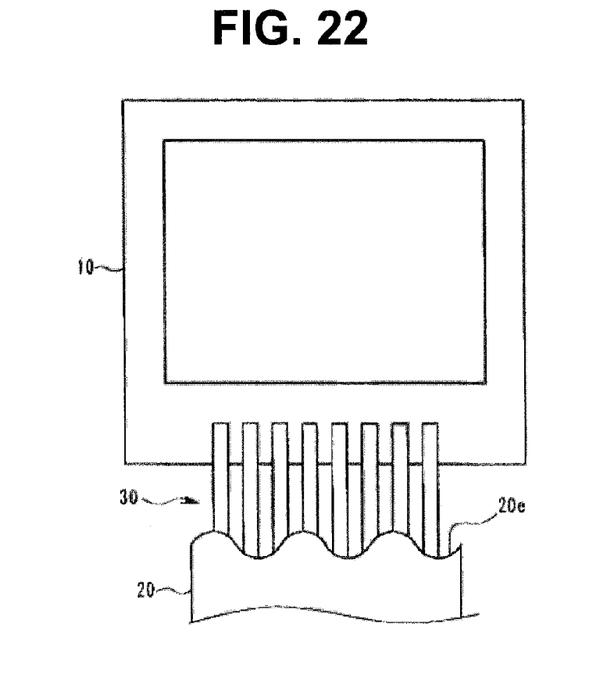
FIG. 22 illustrates the shape of the end face of the circuit substrate according to the fourth embodiment.

In the present embodiment, as shown in FIG. 21 or FIG. 22, a region which is not perpendicular to the extending direction of the lead group 30 is formed on a part or entirety of the end face 20e of the circuit substrate 20, from which the lead group 30 is extended.

Specifically, in the example shown in FIG. 21, the entirety of the end face 20e is formed as a plane intersecting, at a predetermined angle, with the direction perpendicular to the extending direction of the lead group 30. In addition, in the example shown in FIG. 22, the end face 20e is formed as a corrugated curved surface, to thereby form a region which is not perpendicular to the extending direction of the lead group 30.

A part or entirety of the end face 20e is thus configured by the surface which is not perpendicular to the extending direction of the lead group 30, thereby capable of increasing the surface area of the end face 20e without increasing the width of the end face 20e. That is, according to the present embodiment, the area of the end face 20e to which the adhesive 41 is applied can be increased, which enables the bonding strength between the image pickup device 10 and the circuit substrate 20 with the adhesive 41 to be increased.

Note that the present embodiment is not limited to the above-described embodiments, and can be modified as needed in a range without departing from the gist or the concept of the invention which can be read from claims and throughout the specification. Also an image pickup unit for endoscope modified as such is included in the technical range of the present invention.

What is claimed is:

1. An image pickup unit for endoscope, the image pickup unit comprising:
   an image pickup device having a plurality of electrode pads arranged on a front face of the image pickup device, and
   a circuit substrate having a front end face, the circuit substrate having a plurality of leads extending from the end face towards the image pickup device, a distal end portion of the plurality of leads being respectively bonded to the plurality of electrode pads,
   wherein the end face of the circuit substrate is disposed more rearward than a rear face of the image pickup device,
   the plurality of leads includes a first lead, the first lead being at least one of a lead connected to an image pickup device reference electric potential and a dummy lead which does not include an electrical function, the plurality of leads also including a second lead, and
   a shortest distance between the first lead and an edge portion where the rear face and a side face of the image pickup device intersect is shorter than a shortest distance between the second lead and the edge portion, wherein
   the first lead is a flying lead formed by a conductive layer disposed on a first face of the circuit substrate, and
   the second lead is a flying lead formed by a conductive layer disposed on a second face of the circuit substrate, the second face being further from the central axis of the image pickup unit for endoscope than the first face.

2. The image pickup unit for endoscope according to claim 1, wherein the second lead is a lead for inputting and outputting a signal of the image pickup device.

3. An image pickup unit for endoscope, the image pickup unit comprising:
   an image pickup device having a plurality of electrode pads arranged on a front face of the image pickup device, and
   a circuit substrate having a front end face, the circuit substrate having a plurality of leads extending from the end face towards the image pickup device, a distal end portion of the plurality of leads being respectively bonded to the plurality of electrode pads,
   wherein the end face of the circuit substrate is disposed more rearward than a rear face of the image pickup device,
   the plurality of leads includes a first lead, the first lead being at least one of a lead connected to an image pickup device reference electric potential and a dummy lead which does not include an electrical function, the plurality of leads also including a second lead, and
   a shortest distance between the first lead and an edge portion where the rear face and a side face of the image pickup device intersect is shorter than a shortest distance between the second lead and the edge portion, wherein
   the first lead and second lead are flying leads formed respectively by conductive layers disposed on a face of the circuit substrate, and
   the first lead is bent in a shape different from a bent shape of the second lead such that the first lead has a shape which takes a route to the electrode pads, the route being closer to the edge portion than a route of the second lead is to the edge portion.

4. The image pickup unit for endoscope according to claim 3, wherein the second lead is a lead for inputting and outputting a signal of the image pickup device.

\* \* \* \* \*